(12) United States Patent
Patti et al.

(10) Patent No.: US 7,115,264 B2
(45) Date of Patent: Oct. 3, 2006

(54) MONOCLONAL ANTIBODIES TO THE FIBRONECTIN BINDING PROTEIN AND METHOD OF USE IN TREATING OR PREVENTING INFECTIONS

(75) Inventors: Joseph M. Patti, Cumming, GA (US); Pratisksha Patel, Marietta, GA (US); Andrea Hall, Acworth, GA (US); Paul Domanski, Atlanta, GA (US); Peter Syribeys, Decatur, GA (US); Jeff T. Hutchins, Cumming, GA (US)

(73) Assignee: INHIBITEX, Alpharetta, GA (US)

( * ) Notice: Subject to any disclaimer, the term of this patent is extended or adjusted under 35 U.S.C. 154(b) by 0 days.

(21) Appl. No.: 10/287,821

(22) Filed: Nov. 5, 2002

(65) Prior Publication Data

US 2003/0153022 A1  Aug. 14, 2003

Related U.S. Application Data (60) Provisional application No. 60/330,964, filed on Nov. 5, 2001.

(51) Int. Cl.
*A61K 39/40* (2006.01)

(52) U.S. Cl. ............................... 424/165.1; 424/130.1; 424/135.1; 424/141.1; 424/142.1; 424/150.1; 424/165.1; 424/243.1; 435/975; 435/7.1; 530/387.3; 530/387.1; 530/388.15; 530/388.1

(58) Field of Classification Search ............. 530/387.3, 530/388.15, 387.1, 388.1; 424/130.1, 135.1, 424/141.1, 142.1, 150.1, 165.1, 243.1; 435/975, 435/7.2, 7.1

See application file for complete search history.

(56) References Cited

U.S. PATENT DOCUMENTS

| | | | |
|---|---|---|---|
| 4,784,989 A | 11/1988 | Hook et al. |
| 5,175,096 A | 12/1992 | Hook et al. |
| 5,189,015 A | 2/1993 | Hook et al. |
| 5,320,951 A | 6/1994 | Hook et al. |
| 5,416,021 A | 5/1995 | Hook et al. |
| 5,440,014 A | 8/1995 | Hook et al. |
| 5,571,514 A | 11/1996 | Hook et al. |
| 5,648,240 A | 7/1997 | Hook et al. |
| 5,652,217 A | 7/1997 | Hook et al. |
| 5,770,702 A | 6/1998 | Hook et al. |
| 5,789,549 A | 8/1998 | Hook et al. |
| 5,840,846 A | 11/1998 | Hook et al. |
| 5,858,709 A | 1/1999 | Hodgson et al. |
| 5,955,078 A | 9/1999 | Burnham et al. |
| 6,288,214 B1 | 9/2001 | Hook et al. |

FOREIGN PATENT DOCUMENTS

| | | |
|---|---|---|
| EP | 0 294 349 | 12/1988 |
| EP | 0 342 173 | 11/1989 |
| WO | WO 92/02555 | 2/1992 |
| WO | WO 94/18327 | 8/1994 |
| WO | WO 96/04380 | 2/1996 |
| WO | WO 96/04381 | 2/1996 |
| WO | WO 98/31389 | 7/1998 |
| WO | 01/226682 | * 4/2001 |

OTHER PUBLICATIONS

Campbell, A. Laboratory Techniques in Biochemistry and Molecular Biology. 1984. p. 186-187.*
Jonsson et al. Eur.J.Biochem. 1991. 202: 1041-8.*
Signas et al. Proc.Nat.Acad.Sci. USA. 1989. 86: 699-703.*
Sun et al., Identification of D Motif Epitopes in *Staphylococcus aureus* Fibronectin-Binding Protein . . . , Infection and Immunity, Feb. 1997, vol. 65, No. 2, pp. 537-543.
Molinari et al., "The Fibronectin-Binding Protein of *Streptococcus pyogenes*, Sfbl, Is Involved in the Internalization of Group A . . . ", Infection and Immunity, Apr. 1997, vol. 65, No. 4, pp. 1357-1363.
Huff et al., "Interaction of N-terminal Fragments of Fibronectin with Synthetic and Recombinant D Motifs . . . ", vol. 269, No. 22, Issue of Jun. 3, 1994, pp. 15563-15570.
Brennan et al., "Immunogenicity of peptides derived from a fibronectin-binding protein of *S. aureus* expressed . . . ", Elsevier, Vaccine 17 (1999), pp. 1846-1857.
Rennermalm et al., Vaccine, May 14, 2001, 19(25-26), pp. 3376-3386 (Abstract).

* cited by examiner

*Primary Examiner*—Jennifer E. Graser
(74) *Attorney, Agent, or Firm*—B. Aaron Schulman; Stites & Harbison PLLC (57) ABSTRACT

Monoclonal antibodies which can bind to the Fnbp protein of *Staphylococcus aureus* and which are generated from a peptide from the D2 region of fibronectin binding protein B (Fnbp) of *S. aureus* are provided which can be useful in the treatment and protection against infection from staphylococcal bacteria such as *Staphylococcus aureus*. The monoclonal antibodies of the invention are advantageous in that they bind *S. aureus* in high affinity and thus can be useful in the prevention of the adherence of staph bacteria to host cells by impairing or inhibiting the ability of *S. aureus* Fnbp to bind to fibronectin. Kits and methods of utilizing the monoclonal antibodies of the invention are also provided.

18 Claims, 3 Drawing Sheets

SEQUENCE LISTING

<160> NUMBER OF SEQ ID NOS: 2

<210> SEQ ID NO 1
<211> LENGTH: 30
<212> TYPE: PRT
<213> ORGANISM: Staphylococcus aureus

<400> SEQUENCE: 1

Gly Gln Asn Asn Gly Asn Gln Ser Phe Glu Glu Asp Thr Glu Lys Asp
1               5                   10                  15

Lys Pro Lys Tyr Glu Gln Gly Gly Asn Ile Ile Asp Ile Asp
            20                  25                  30

```
<210> SEQ ID NO 2
<211> LENGTH: 31
<212> TYPE: PRT
<213> ORGANISM: Staphylococcus aureus

<400> SEQUENCE: 2

Cys Gly Gln Asn Asn Gly Asn Gln Ser Phe Glu Glu Asp Thr Glu Lys
1               5                   10                  15

Asp Lys Pro Lys Tyr Glu Gln Gly Gly Asn Ile Ile Asp Ile Asp
            20                  25                  30
```

MONOCLONAL ANTIBODIES TO THE FIBRONECTIN BINDING PROTEIN AND METHOD OF USE IN TREATING OR PREVENTING INFECTIONS

CROSS REFERENCE TO RELATED APPLICATIONS

The present application claims the benefit of U.S. provisional application Ser. No. 60/330,964 filed Nov. 5, 2001.

FIELD OF THE INVENTION

The present invention relates in general to antibodies that have been generated against and which can recognize fibronectin binding proteins (Fnbp) from *Staphylococcus aureus* (*S. aureus*), and in particular to monoclonal antibodies generated against the D2 peptide of fibronectin binding protein B (FnbpB), which are capable of recognizing *S. aureus* with high affinity and which are useful in inhibiting the binding of *S. aureus* to fibronectin and thus can be used in methods of treating or preventing infections.

BACKGROUND OF THE INVENTION

*Staphylococcus aureus* is an important pathogen that continues to cause a significant number of community-acquired and nosocomial infections worldwide. The sophisticated interplay between host and bacterium is still not completely understood, however, successful colonization is presumed to be the defining event lead to initiation of an infection. MSCRAMM® (Microbial Surface Components Recognizing Adhesive Matrix Molecules) proteins are a family of cell-surface adhesins that recognize and specifically bind to distinct components within host tissues or to serum-conditioned implanted biomaterials such as catheters, artificial joints, and vascular grafts. Once *S. aureus* have successfully adhered and colonized host tissues, expression of specific genes are altered resulting in phenotype that is more resistant to antimicrobials.

The dramatic increase in methicillin-resistant bacteria coupled with the recent emergence of vancomycin-resistant isolates have accelerated and broadened the interest in developing novel therapeutics against *S. aureus*. MSCRAMM® proteins provide an excellent target for immunological attack by antibodies. MSCRAMM® protein antibodies exhibit at least two biological properties; initially the highly specific antibodies prevent microbial adherence or recolonization of host tissues or biomaterials and secondly the increased level of MSCRAMM® protein antibodies bound to the cell wall facilitate a rapid clearance of the organism through opsonophagocytosis.

However, it has still remained a problem to identify and utilize the information concerning MSCRAMMs® from *S. aureus*, such as the fibronectin binding protein, to generate effective monoclonal antibodies because of the variability in the binding properties of the different MSCRAMMs® and their role in infectivity and spread of bacterial infections. Recently, Brennan and Colleagues, Vaccine 17:1846–1857 (1999) demonstrated that the D-2 peptide from FnbpB expressed on the surface of two different plant viruses were highly immunogenic in mice and rats. They later showed that this polyclonal antisera was protective against endocarditis and weight loss associated with *S. aureus* bacteraemia (Rennermalm et.al. Vaccine 19:3376–3383 (2001)). On the other hand, it has been a problem to develop monoclonal antibodies which can be generated from the fibronectin binding proteins and/or their active fragments and which can be use to inhibit or impair the binding of staphylococcal Fnbp to fibronectin and thus be useful in methods of preventing or treating staphylococcal infections. It has thus remained a highly desirable goal in the field of infectious diseases to develop monoclonal antibodies and other compositions which are successful in treating and preventing a wide variety of staph infections, particularly by inhibiting or impairing the bacteria's ability to bind to fibronectin.

SUMMARY OF THE INVENTION

Accordingly, it is an object of the present invention to provide monoclonal antibodies that can bind to *S. aureus* with high affinity and which can recognize and bind to *S. aureus* fibronectin binding proteins including fibronectin binding protein A (FnbpA) and fibronectin binding protein B (FnbpB) and thus be useful in methods to treat, prevent or diagnose staphylococcal infections.

It is also an object of the present invention to provide monoclonal antibodies which are able to bind Fnbp, and which are generated from the binding subdomains of the *S. aureus* FnbpB protein, including the D2 peptide, or from other active portions thereof, to be utilized in methods of inhibiting the binding of staph bacteria to fibronectin and thus be useful in methods of treating or protecting against staphylococcal infections.

It is also an object of the present invention to provide monoclonal antibodies to the D2 peptide from FnbpB which can be useful in preventing adherence of Staphylococcal bacteria by inhibiting or impairing the binding of the Fnbp protein to fibronectin.

It is a further object of the present invention to provide antibodies and antisera which can recognize the fibronectin binding domain of staph fibronectin binding proteins such as the FnbpA protein and the FnbpB protein, and which can thus be useful in methods of treating, preventing, identifying or diagnosing staphylococcal infections.

It is a further object of the invention to provide synthetic peptides and compositions from the D2 region of FnbpB which can be used to generate antibodies useful to treat or prevent a staphylococcal infection.

These and other objects are provided by virtue of the present invention which comprises the generation and use of monoclonal antibodies which can recognize the *S. aureus* Fnbp proteins and/or their binding subdomains, for the treatment or prevention of *Staphylococcus* infections. The present application also comprises the generation of monoclonal antibodies against the D2 peptide of the fibronectin binding protein B from *S. aureus* which binds *S. aureus* with high affinity as reflected in the data presented herein. The discovery and isolation of these monoclonal antibodies in accordance with the present invention can thus be used to impair or inhibit binding of *S. aureus* to fibronectin and thus be useful in methods or treating or preventing staph infections. In accordance with the invention, suitable compositions and passive vaccines based on the monoclonal antibodies of the invention, as well as methods for their use, are also contemplated.

These embodiments and other alternatives and modifications within the spirit and scope of the disclosed invention will become readily apparent to those skilled in the art from reading the present specification and/or the references cited herein, all of which are incorporated by reference.

DETAILED DESCRIPTION OF THE PREFERRED EMBODIMENTS

In accordance with the present invention, there are provided monoclonal antibodies which can bind to the fibronectin binding proteins FnbpA and FnbpB, surface localized proteins that are expressed by virtually every S. aureus strain. In the preferred method of generating these monoclonal antibodies, they are raised against a D2 peptide of the FnbpB protein, and more specifically raised against a peptide encoding the first 30 amino acids of the D2 region. The monoclonal antibodies in accordance with the invention have been shown to have high affinity for binding to S. aureus, and more particularly can bind the fibronectin binding proteins from S. aureus, including FnbpA and FnbpB.

Accordingly, the present invention relates to an isolated and/or purified monoclonal antibody which can bind to the FnbpA and FnbpB proteins and/or their binding subdomains, and which thus can be useful in methods of inhibiting adherence of S. aureus to host cells and thus treat or prevent a staphylococcal infection when used in amounts effective to prevent or treat such infections. These monoclonal antibodies may be produced using, e.g., the method of Kohler and Milstein, Nature 256:495–497 (1975), or other suitable ways known in the field, and in addition can be prepared as chimeric, humanized, or human monoclonal antibodies in ways that would be well known in this field. Still further, monoclonal antibodies may be prepared from a single chain, such as the light or heavy chains, and in addition may be prepared from active fragments of an antibody which retain the binding characteristics (e.g., specificity and/or affinity) of the whole antibody. By active fragments is meant an antibody fragment which has the same binding specificity as a complete antibody which binds to a fibronectin binding protein, and the term "antibody" as used herein is meant to include said fragments. Additionally, antisera prepared using monoclonal or polyclonal antibodies in accordance with the invention are also contemplated and may be prepared in a number of suitable ways as would be recognized by one skilled in the art.

As indicated above, antibodies in accordance with the invention may be prepared in a number of suitable ways that would be well known in the art, such as the well-established Kohler and Milstein method described above which can be utilized to generate monoclonal antibodies. In one such preferred method, a D2 peptide encoding the first 30 amino acids of the D2 region (GQNNGNQSFEEDTEKDKP-KYEQGGNIIDID) (SEQ ID NO:1) was synthesized using a peptide synthesizer, and this peptide was synthesized to contain a cysteine at the N-terminus. This D2 peptide had a resulting amino acid sequence of C-GQNNGNQS-FEEDTEKDKPKYEQGGNIIDID) (SEQ ID NO:2).

In the preferred method of generating the monoclonal antibody in accordance with the invention, the D2 peptide is used to generate a panel of murine monoclonal antibodies using RIMMS as described by Kilpatrick et al., Hybridoma 16(4):381–389 (1997), hereby incorporated by reference. Alternatively, the monoclonal antibodies may be generated by subcutaneously immunizing Balb/C mice in a series of immunizations such as shown in the table below:

|  | Day | Amount (mg) | Route | Adjuvant |
| --- | --- | --- | --- | --- |
| RIMMS Injection |  |  |  |  |
| #1 | 0 | 5 | Subcutaneous | FCA/RIBI |
| #2 | 2 | 1 | Subcutaneous | FCA/RIBI |
| #3 | 4 | 1 | Subcutaneous | FCA/RIBI |
| #4 | 7 | 1 | Subcutaneous | FCA/RIBI |
| #5 | 9 | 1 | Subcutaneous | FCA/RIBI |
| Conventional Injection |  |  |  |  |
| Primary | 0 | 5 | Subcutaneous | FCA |
| Boost #1 | 14 | 1 | Intraperitoneal | RIBI |
| Boost #2 | 28 | 1 | Intraperitoneal | RIBI |
| Boost #3 | 42 | 1 | Intraperitoneal | RIBI |

In this procedure, at the time of sacrifice (RIMMS) or seven days after a boost (conventional), serum is collected and titered in ELISA assays against DUD4-His(6x) from a fibronectin binding protein such as FnbpA or on whole cells, e.g., from S. aureus. At a suitable period after the final boost, e.g., three days, the spleens from lymph nodes may be removed, teased to single cell suspension and the lymphocytes can be harvested. The lymphocytes may then be fused to a suitable myeloma cell line such as P3X63Ag8.653 (ATCC #CRL-1580). Cell fusion, subsequent plating and feeding can be performed according to the "Production of Monoclonal Antibodies" protocol from the treatise "Current Protocols in Immunology", Chapter 2, Unit 2, incorporated herein by reference. Any clones generated from the fusion are then screened for specific anti-D2 peptide antibody production using a standard ELISA assay, and positive clones may be expanded and tested further, such as through tests of antibody binding to whole S. aureus or other tests regarding a kinetic analysis of the antibody binding. Through the method of the present invention, monoclonal antibodies can thus be generated from D2 peptide isolates which will be able to bind the fibronectin binding proteins from S. aureus and thus be useful in inhibiting S. aureus adherence to host cells.

Although production of antibodies as indicated above is preferably carried out using synthetic or recombinantly produced forms of the D2 peptide regions, antibodies may be generated from natural isolated and purified D2 peptides or active fragments thereof. Still other conventional ways are available to generate the Fnbp antibodies of the present invention using recombinant or natural purified Fnbp proteins or their active regions, as would be recognized by one skilled in the art.

As would be recognized by one skilled in the art, the antibodies of the present invention may also be formed into suitable pharmaceutical compositions for administration to a human or animal patient in order to treat or prevent an infection caused by staphylococcal bacteria. Pharmaceutical compositions containing the antibodies of the present invention, or effective fragments thereof, may be formulated in combination with any suitable pharmaceutical vehicle, excipient or carrier that would commonly be used in this art, including such as saline, dextrose, water, glycerol, ethanol, other therapeutic compounds, and combinations thereof. As one skilled in this art would recognize, the particular vehicle, excipient or carrier used will vary depending on the patient and the patient's condition, and a variety of modes of administration would be suitable for the compositions of the invention, as would be recognized by one of ordinary skill in this art. Suitable methods of administration of any pharmaceutical composition disclosed in this application include, but are not limited to, topical, oral, anal, vaginal, intravenous, intraperitoneal, intramuscular, subcutaneous, intranasal and intradermal administration.

For topical administration, the composition is formulated in the form of an ointment, cream, gel, lotion, drops (such as eye drops and ear drops), or solution (such as mouthwash). Wound or surgical dressings, sutures and aerosols may be impregnated with the composition. The composition may contain conventional additives, such as preservatives, solvents to promote penetration, and emollients. Topical formulations may also contain conventional carriers such as cream or ointment bases, ethanol, or oleyl alcohol.

Additional forms of antibody compositions, and other information concerning compositions, methods and applications with regard to other MSCRAMM®s will generally also be applicable to the present invention involving antibodies to the ClfA MSCRAMM™ and are disclosed, for example, in U.S. Pat. No. 6,288,214 (Hook et al.), incorporated herein by reference.

The antibody compositions of the present invention which are generated against a peptide from the D2 region of the FnbpB protein from *S. aureus* (SEQ ID NO: 3) may also be administered with a suitable adjuvant in an amount effective to enhance the immunogenic response against the conjugate. For example, suitable adjuvants may include alum (aluminum phosphate or aluminum hydroxide), which is used widely in humans, and other adjuvants such as saponin and its purified component Quil A, Freund's complete adjuvant, RIBBI adjuvant, and other adjuvants used in research and veterinary applications. Still other chemically defined preparations such as muramyl dipeptide, monophosphoryl lipid A, phospholipid conjugates such as those described by Goodman-Snitkoff et al. *J. Immunol.* 147:410–415 (1991) and incorporated by reference herein, encapsulation of the conjugate within a proteoliposome as described by Miller et al., *J. Exp. Med.* 176:1739–1744 (1992) and incorporated by reference herein, and encapsulation of the protein in lipid vesicles such as Novasome™ lipid vesicles (Micro Vescular Systems, Inc., Nashua, N.H.) may also be useful.

In any event, the antibody compositions of the present invention will thus be useful for interfering with, modulating, or inhibiting binding interactions between the Fnbp proteins, such as FnbpA and FnbpB, on staphylococcal bacteria and fibronectin on host cells and tissues, and will thus have particular applicability in developing compositions and methods of preventing or treating staphylococcal infection, and in inhibiting binding of staphylococcal bacteria to host tissue and/or cells.

In accordance with the present invention, methods are provided for preventing or treating a staphylococcal infection which comprise administering an effective amount of the monoclonal antibody of the present invention as described above in amounts effective to treat or prevent the infection. In addition, these monoclonal antibodies have been shown to have high affinity in binding of staphylococcal bacteria, and thus should be effective in treating or preventing infection from staph bacteria such as *S. aureus*.

Accordingly, in accordance with the invention, administration of the antibodies of the present invention in any of the conventional ways described above (e.g., topical, parenteral, intramuscular, etc.), and will thus provide an extremely useful method of treating or preventing staphylococcal infections in human or animal patients. By effective amount is meant that level of use, such as of an antibody titer, that will be sufficient to either prevent adherence of the bacteria, to inhibit binding of staph bacteria to host cells and thus be useful in the treatment or prevention of a staph infection. As would be recognized by one of ordinary skill in this art, the level of antibody titer needed to be effective in treating or preventing staphylococcal infection will vary depending on the nature and condition of the patient, and/or the severity of the pre-existing staphylococcal infection.

In addition to the use of antibodies to the D2 peptide to treat or prevent *S. aureus* infection as described above, the present invention contemplates the use of these antibodies in a variety of ways, including the detection of the presence of *S. aureus* to diagnose a staph infection, whether in a patient or on medical equipment which may also become infected. In accordance with the invention, a preferred method of detecting the presence of staph infections involves the steps of obtaining a sample suspected of being infected by one or more staphylococcal bacteria species or strains, such as a sample taken from an individual, for example, from one's blood, saliva, tissues, bone, muscle, cartilage, or skin. The cells can then be lysed, and the DNA extracted, precipitated and amplified. Following isolation of the sample, diagnostic assays utilizing the antibodies of the present invention may be carried out to detect the presence of *S. aureus*, and such assay techniques for determining such presence in a sample are well known to those skilled in the art and include methods such as radioimmunoasssay, Western blot analysis and ELISA assays. In general, in accordance with the invention, a method of diagnosing an *S. aureus* infection is contemplated wherein a sample suspected of being infected with *S. aureus* infection has added to it the monoclonal antibody in accordance with the present invention, and *S. aureus* is indicated by antibody binding to the Fnbp proteins in the sample.

Accordingly, antibodies in accordance with the invention may be used for the specific detection of staphylococcal map proteins, for the prevention of infection from staph bacteria, for the treatment of an ongoing infection, or for use as research tools. The term "antibodies" as used herein includes monoclonal, polyclonal, chimeric, single chain, bispecific, simianized, and humanized or primatized antibodies as well as Fab fragments, such as those fragments which maintain the binding specificity of the antibodies to the Fnbp proteins, including the products of an Fab immunoglobulin expression library. Accordingly, the invention contemplates the use of single chains such as the variable heavy and light chains of the antibodies as will be set forth below. Generation of any of these types of antibodies or antibody fragments is well known to those skilled in the art. In the present case, monoclonal antibodies to Fnbp proteins have been generated against a peptide from the D2 region of FnbpB have been isolated and shown to have high affinity to *S. aureus* and thus can be used in methods to protect against staphylococcal infection.

Any of the above described antibodies may be labeled directly with a detectable label for identification and quantification of staph bacteria. Labels for use in immunoassays are generally known to those skilled in the art and include enzymes, radioisotopes, and fluorescent, luminescent and chromogenic substances, including colored particles such as colloidal gold or latex beads. Suitable immunoassays include enzyme-linked immunosorbent assays (ELISA).

Alternatively, the antibody may be labeled indirectly by reaction with labeled substances that have an affinity for immunoglobulin. The antibody may be conjugated with a second substance and detected with a labeled third substance having an affinity for the second substance conjugated to the antibody. For example, the antibody may be conjugated to biotin and the antibody-biotin conjugate detected using labeled avidin or streptavidin. Similarly, the antibody may be conjugated to a hapten and the antibody-hapten conjugate detected using labeled anti-hapten antibody. These and other methods of labeling antibodies and assay conjugates are well known to those skilled in the art.

Antibodies to Fnbp as described above may also be used in production facilities or laboratories to isolate additional quantities of the proteins, such as by affinity chromatography. For example, the antibodies of the invention may also be utilized to isolate additional amounts of the Fnbp proteins or their active fragments.

The isolated antibodies of the present invention, or active fragments thereof, may also be utilized in the development of vaccines for passive immunization against staph infections. Further, when administered as pharmaceutical composition to a wound or used to coat medical devices or polymeric biomaterials in vitro and in vivo, the antibodies of the present invention, may be useful in those cases where there is a previous staph infection because of the ability of this antibody to further restrict and inhibit *S. aureus* binding to fibronectin and thus limit the extent and spread of the infection. In addition, the antibody may be modified as necessary so that, in certain instances, it is less immunogenic in the patient to whom it is administered. For example, if the patient is a human, the antibody may be "humanized" by transplanting the complimentarity determining regions of the hybridoma-derived antibody into a human monoclonal antibody as described, e.g., by Jones et al., *Nature* 321: 522–525 (1986) or Tempest et al. *Biotechnology* 9:266–273 (1991) or "veneered" by changing the surface exposed murine framework residues in the immunoglobulin variable regions to mimic a homologous human framework counterpart as described, e.g., by Padlan, Molecular Imm. 28:489–498 (1991), these references incorporated herein by reference. Even further, when so desired, the monoclonal antibodies of the present invention may be administered in conjunction with a suitable antibiotic to further enhance the ability of the present compositions to fight bacterial infections.

Medical devices or polymeric biomaterials to be coated with the antibodies, proteins and active fragments described herein include, but are not limited to, staples, sutures, replacement heart valves, cardiac assist devices, hard and soft contact lenses, intraocular lens implants (anterior chamber or posterior chamber), other implants such as corneal inlays, kerato-prostheses, vascular stents, epikeratophalia devices, glaucoma shunts, retinal staples, scleral buckles, dental prostheses, thyroplastic devices, laryngoplastic devices, vascular grafts, soft and hard tissue prostheses including, but not limited to, pumps, electrical devices including stimulators and recorders, auditory prostheses, pacemakers, artificial larynx, dental implants, mammary implants, penile implants, cranio/facial tendons, artificial joints, tendons, ligaments, menisci, and disks, artificial bones, artificial organs including artificial pancreas, artificial hearts, artificial limbs, and heart valves; stents, wires, guide wires, intravenous and central venous catheters, laser and balloon angioplasty devices, vascular and heart devices (tubes, catheters, balloons), ventricular assists, blood dialysis components, blood oxygenators, urethral/ureteral/urinary devices (Foley catheters, stents, tubes and balloons), airway catheters (endotracheal and tracheostomy tubes and cuffs), enteral feeding tubes (including nasogastric, intragastric and jejunal tubes), wound drainage tubes, tubes used to drain the body cavities such as the pleural, peritoneal, cranial, and pericardial cavities, blood bags, test tubes, blood collection tubes, vacutainers, syringes, needles, pipettes, pipette tips, and blood tubing.

It will be understood by those skilled in the art that the term "coated" or "coating", as used herein, means to apply the antibody or active fragment, or pharmaceutical composition derived therefrom, to a surface of the device, preferably an outer surface that would be exposed to streptococcal bacterial infection. The surface of the device need not be entirely covered by the protein, antibody or active fragment.

In a preferred embodiment, the antibodies may also be used as a passive vaccine which will be useful in providing suitable antibodies to treat or prevent a staphylococcal infection. As would be recognized by one skilled in this art, a vaccine may be packaged for administration in a number of suitable ways, such as by parenteral (i.e., intramuscular, intradermal or subcutaneous) administration or nasopharyngeal (i.e., intranasal) administration. One such mode is where the vaccine is injected intramuscularly, e.g., into the deltoid muscle, however, the particular mode of administration will depend on the nature of the bacterial infection to be dealt with and the condition of the patient. The vaccine is preferably combined with a pharmaceutically acceptable carrier to facilitate administration, and the carrier is usually water or a buffered saline, with or without a preservative. The vaccine may be lyophilized for resuspension at the time of administration or in solution.

The preferred dose for administration of an antibody composition in accordance with the present invention is that amount will be effective in preventing of treating a staphylococcal infection, and one would readily recognize that this amount will vary greatly depending on the nature of the infection and the condition of a patient. As indicated above, an "effective amount" of antibody or pharmaceutical agent to be used in accordance with the invention is intended to mean a nontoxic but sufficient amount of the agent, such that the desired prophylactic or therapeutic effect is produced. As will be pointed out below, the exact amount of the antibody or a particular agent that is required will vary from subject to subject, depending on the species, age, and general condition of the subject, the severity of the condition being treated, the particular carrier or adjuvant being used and its mode of administration, and the like. Accordingly, the "effective amount" of any particular antibody composition will vary based on the particular circumstances, and an appropriate effective amount may be determined in each case of application by one of ordinary skill in the art using only routine experimentation. The dose should be adjusted to suit the individual to whom the composition is administered and will vary with age, weight and metabolism of the individual. The compositions may additionally contain stabilizers or pharmaceutically acceptable preservatives, such as thimerosal (ethyl(2-mercaptobenzoate-S)mercury sodium salt) (Sigma Chemical Company, St. Louis, Mo.).

When used with suitable labels or other appropriate detectable biomolecule or chemicals, the monoclonal antibodies described herein are useful for purposes such as in vivo and in vitro diagnosis of staphylococcal infections or detection of staphylococcal bacteria. Laboratory research may also be facilitated through use of such antibodies. Various types of labels and methods of conjugating the labels to the antibodies of the invention are well known to those skilled in the art, such as the ones set forth below.

For example, the antibody can be conjugated (directly or via chelation) to a radiolabel such as, but not restricted to, $^{32}P$, $^{3}H$, $^{14}C$, $^{35}S$, 125I, or $^{131}I$. Detection of a label can be by methods such as scintillation counting, gamma ray spectrometry or autoradiography. Bioluminescent labels, such as derivatives of firefly luciferin, are also useful. The bioluminescent substance is covalently bound to the protein by conventional methods, and the labeled protein is detected when an enzyme, such as luciferase, catalyzes a reaction with ATP causing the bioluminescent molecule to emit photons of light. Fluorogens may also be used to label proteins. Examples of fluorogens include fluorescein and derivatives, phycoerythrin, allo-phycocyanin, phycocyanin, rhodamine, and Texas Red. The fluorogens are generally detected by a fluorescence detector.

The location of a ligand in cells can be determined by labeling an antibody as described above and detecting the label in accordance with methods well known to those skilled in the art, such as immunofluorescence microscopy using procedures such as those described by Warren et al. (*Mol. Cell. Biol.*, 7: 1326–1337, 1987).

As indicated above, the monoclonal antibodies of the present invention, or active portions or fragments thereof, are particularly useful for interfering with the initial physical interaction between a staphylococcal pathogen responsible for infection and a mammalian host, such as the adhesion of the bacteria to mammalian extracellular matrix proteins such as fibronectin, and this interference with physical interaction may be useful both in treating patients and in preventing or reducing bacteria infection on in-dwelling medical devices to make them safer for use.

In another embodiment of the present invention, a kit which may be useful in isolating and identifying staphylococcal bacteria and infection is provided which comprises the antibodies of the present invention in a suitable form, such as lyophilized in a single vessel which then becomes active by addition of an aqueous sample suspected of containing the staphylococcal bacteria. Such a kit will typically include a suitable container for housing the antibodies in a suitable form along with a suitable immunodetection reagent which will allow identification of complexes binding to the Fnbp antibodies of the invention. For example, the immunodetection reagent may comprise a suitable detectable signal or label, such as a biotin or enzyme that produces a detectable color, etc., which normally may be linked to the antibody or which can be utilized in other suitable ways so as to provide a detectable result when the antibody binds to the antigen.

In short, the antibodies of the present invention which bind to the FnbpA and FnbpB proteins or active fragments thereof are thus extremely useful in treating or preventing staphylococcal infections in human and animal patients and in medical or other in-dwelling devices. Accordingly, the present invention relates to methods of identifying and isolating antibodies which can bind to Fnbp and which can be used in methods of treatment of staph infections which involve opsonophagocytic killing of the bacteria. Antibodies which are identified and/or isolated using the present method, such as the anti-D2 antibody which can bind to the Fnbp proteins such as FnbpA and FnbpB and which can prevent or treat a staph infection thus is part of the present invention

EXAMPLES

The following examples are provided which exemplify aspects of the preferred embodiments of the present invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparation of Monoclonal Antibodies to the D2 Peptide

This example describes the discovery, production and characterization of a monoclonal antibody against the fibronectin binding proteins FnbpA and FnbpB, surface localized proteins that are expressed by virtually every *S. aureus* strain. Data presented here clearly demonstrate that monoclonal antibodies against a D2 peptide of FnbpB binds *S. aureus* with high affinity.

Using a peptide synthesizer, a peptide encoding the first 30 amino acids of the D2 region (GQNNGNQSFEEDTEKDKPKYEQGGNIIDID) (SEQ ID NO:1) was synthesized containing a cysteine at the N-terminus (C-GQNNGNQSFEEDTEKDKPKYEQGGNIIDID) (SEQ ID NO:2). For Immunization purposes, this peptide was conjugated to ovalbumin via the N-terminal cysteine.

Monoclonal Antibody Production

The D2 peptide described above was used to generate a panel of murine monoclonal antibodies as described by Kilpatrick, et al. (Rapid development of affinity matured monoclonal antibodies using RIMMS. 1997. Hybridoma 16(4):381–389). Alternatively, a group of Balb/C mice received a series of subcutaneous immunizations as described below in Table 1:

TABLE 1

|  | Day | Amount (mg) | Route | Adjuvant |
| --- | --- | --- | --- | --- |
| RIMMS Injection |  |  |  |  |
| #1 | 0 | 5 | Subcutaneous | FCA/RIBI |
| #2 | 2 | 1 | Subcutaneous | FCA/RIBI |
| #3 | 4 | 1 | Subcutaneous | FCA/RIBI |
| #4 | 7 | 1 | Subcutaneous | FCA/RIBI |
| #5 | 9 | 1 | Subcutaneous | FCA/RIBI |
| Conventional Injection |  |  |  |  |
| Primary | 0 | 5 | Subcutaneous | FCA |
| Boost #1 | 14 | 1 | Intraperitoneal | RIBI |
| Boost #2 | 28 | 1 | Intraperitoneal | RIBI |
| Boost #3 | 42 | 1 | Intraperitoneal | RIBI |

At the time of sacrifice (RIMMS) or seven days after a boost (conventional) serum was collected and titered in ELISA assays against DUD4-His(6×) from FnbpA or on whole cells (*S. aureus*). Three days after the final boost, the spleens or lymph nodes were removed, teased into a single cell suspension and the lymphocytes harvested. The lymphocytes were then fused to the P3X63Ag8.653 myeloma cell line (ATCC #CRL-1580). Cell fusion, subsequent plating and feeding were performed according to the Production of Monoclonal Antibodies protocol from Current Protocols in Immunology (Chapter 2, Unit 2.).

Any clones that were generated from the fusion were then screened for specific anti-D2 peptide antibody production using a standard ELISA assay. Positive clones were expanded and tested further.

Binding to Whole Bacteria

*S. aureus* bacterial samples (strain 67-0) were collected, washed and incubated with Mab F57-010, or media alone (control) after blocking protein A sites with rabbit IgG (50 g/ml). Following incubation with antibody, bacterial cells were incubated with Goat-F(ab')2-Anti-Mouse-F(ab')2-FITC which served as the detection antibody. After antibody labeling, bacterial cells were aspirated through the FACS-caliber flow cytometer to analyze fluorescence emission (excitation: 488, emission: 570). For each bacterial strain, 10,000 events were collected and measured.

Kinetic Analysis

Kinetic analysis was performed on a Biacore 3000 using the Ligand capture method included in the software. A rabbit anti-mouse-Fc antibody (Biacore) was amine coupled to a CM5 chip. Throughout the analysis, the flow rate remained constant at 10 (l/min. Prior to the DUD4-GST injection, test antibody was adsorbed to the chip via RAM-Fc binding. At time 0, DUD4-GST at a concentration of 30 (g/ml was injected over the chip for 3 min followed by 2 minutes of dissociation. This phase of the analysis measured the relative association and disassociation kinetics of the Mab/DUD4-GST interaction. In the second phase of the analysis, the ability of the Mab bound DUD4-GST to interact and bind fibronectin was measured. Fibronectin at a concentration of 100 (g/ml was injected over the chip and after 3 minutes a report point is taken. By this analysis, monoclonal antibodies F57-010 and F61-007 were identified as high affinity binders to DUD4-GST.

Example 2

Use of the Biacore to Select High Affinity Mabs that Block DUD4 Binding to Fibronectin and Bind to *Staphylococcus aureus*

Figure 1:
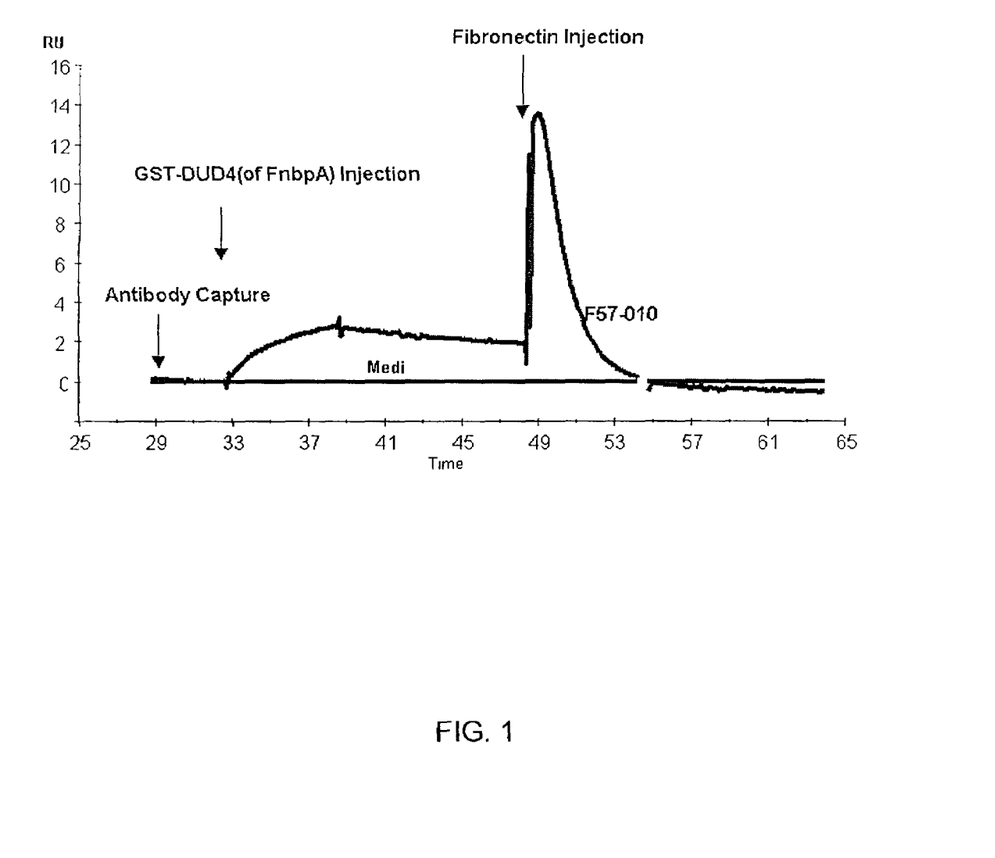
FIG. 1 is a graph of a biacore analysis used to measure DUD4-GST binding and subsequent binding/inhibition of fibronectin when a monoclonal antibody in accordance with the invention (Mab F57-010) or Media alone (as a control) are bound to the chip, as performed using rabbit anti-mouse Fc (RAM-Fc) antibody

A Biacore analysis to measure DUD4-GST binding and subsequent binding/inhibition of fibronectin when Mab F57-10 or Media are bound to the chip was performed using rabbit anti-mouse Fc (RAM-Fc) antibody. The results are shown in FIG. 1. In addition, a flow cytometric analysis of F57-10 binding to *Staphylococcus aureus* strain 67-0 was conducted, and the results are shown in FIG. 2.

Figure 2:
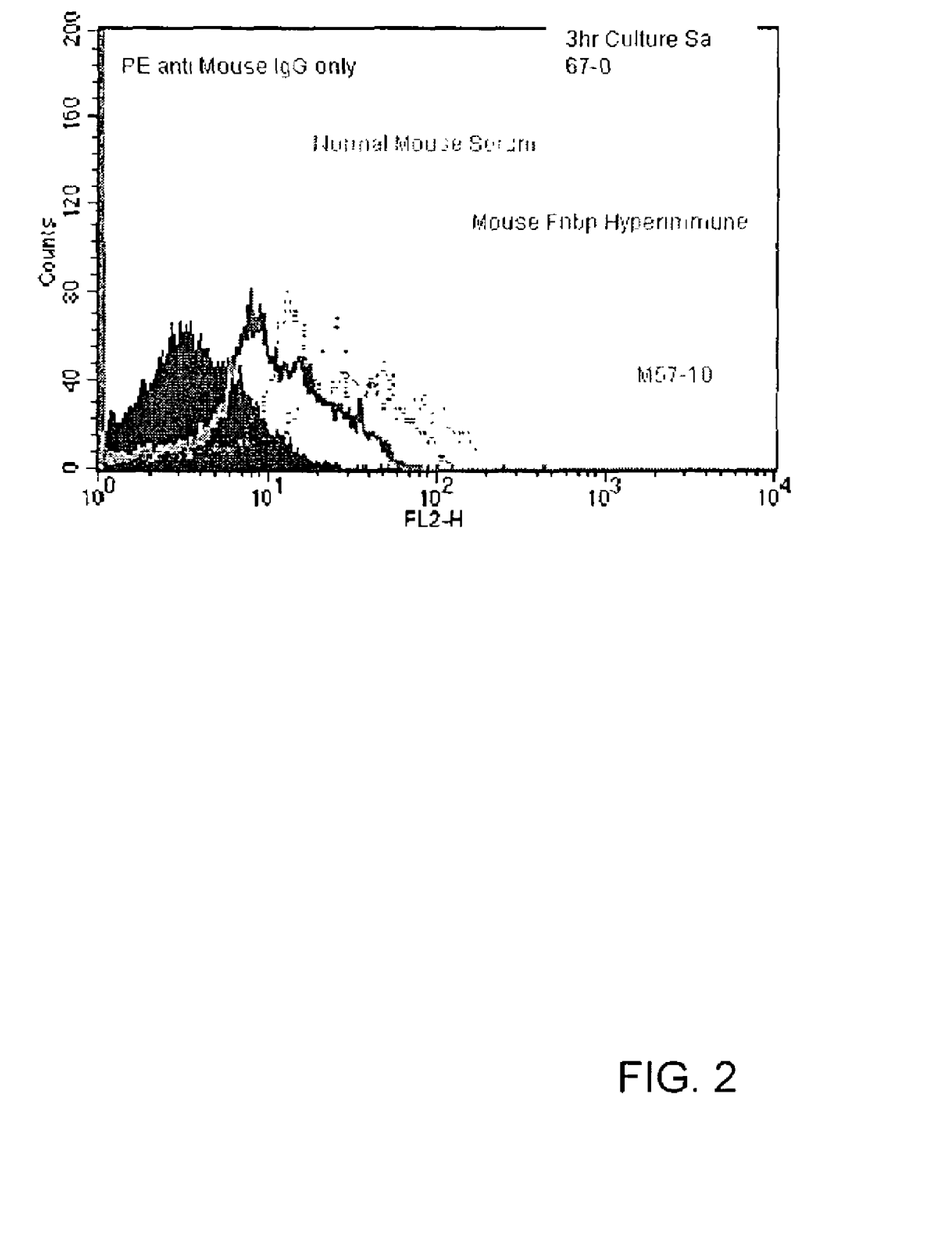
FIG. 2 is a graph of a flow cytometric analysis of monoclonal antibody F57-010 binding to Staphylococcus aureus strain 67-0.

The results represented in FIGS. 1 and 2 with F57-10 demonstrate that a monoclonal antibody with high affinity and selectivity can be generated using the D2 peptide as an immunogen. Accordingly, the monoclonal antibodies of the present invention can be used to prevent binding of *S. aureus* Fnbp to fibronectin, and can thus be useful in methods of treating or preventing *S. aureus* infections.

Example 3

Protective Activity of the Anti-D2 Monoclonal Antibody in a Murine Model of Sepsis The purpose of this example is to characterize the protective effects of the D2 monoclonal antibody, 57-010 compared with the isotype-matched control CRL1771 antibody and FnbpA monoclonal antibody 43-677 using a 0.8 mg dose of antibody and *S. aureus* strain 67-0 in a mouse sepsis model.

Sepsis Model Design

| Species | Strain | Sex | Number | Age* | Weight* | Source |
|---|---|---|---|---|---|---|
| Mice | Balb/C | Female | 90 | 4–5 weeks | 12–16 grams | Taconic Farms, Inc. (Germantown, NY) |

*Estimated range at initiation of study.

Dosing was performed by the administration of an intraperitoneal (i.p.) injection of monoclonal antibody to the appropriate animals (see below). Administration of the antibody was performed approximately 18 hours prior to the intravenous (i.v.) injection of *S. aureus*. Systemic infection was measured using a single parameter (mortality).

| | | TREATMENT | | | | | CHALLENGE | | |
|---|---|---|---|---|---|---|---|---|---|
| Group # | No. of Mice | Antibody | Dose | Route | Frequency | Time Point* | Bacteria | CFU | Volume/ Route |
| 1 | 30 | 57–010 | 0.8 mg. | i.p. | Once | −18 hr. | *S. aureus* 67-0 | ~10$^8$ | 0.1 ml./ i.v. |
| 2 | 30 | 43–677 | 0.8 mg. | | | | | | |
| 3 | 30 | CRL1771 | 0.8 mg. | | | | | | |

*Time points reflect hours post bacterial challenge.

Preparation, Storage and Handling

*Staphylococcus aureus*

MRSA strain 67-0 cells were taken from a frozen glycerol stock and were inoculated onto a single blood agar plate and grown for 24 hours at 37° C. Single colonies were then transferred to new blood agar plates. Eighty plates were inoculated to prepare 50 mls of final frozen stock. The plates were then incubated for 24 hours at 37° C. Following incubation, the colonies were scraped off the surface of each plate into four 50 ml tubes containing 10 mls of 1×PBS (20 plates per tube) while gently vortexing to remove the bacteria from the scraper. An additional 10 mls of 1×PBS was then added to the 10 mls of bacterial suspension, while vigorously vortexing to facilitate separation of any agar debris from the bacteria. The suspension was pelleted by centrifugation, 3500×g at 4° C. for 10 minutes. The bacteria was washed in D-PBS and resuspended in 50 mls of freezing media. The bacterial stock was placed into 1 ml aliquots by snap freezing in an ethanol/dry ice bath and placed in an −80° C. freezer. The concentration (CFU/ml) of the frozen stock was determined by thawing 1 ml aliquot of stock, and preparing serial dilutions from $10^{-5}$ to $10^{-11}$. Dilutions were plated in duplicate on blood agar plates and incubated for 37° C. for 16–18 hours. The CFU/ml was determined (CFU/ml=(average # colonies×dilution factor)/0.050 mls) and averaged for each dilution to determine the average CFU/ml. On the day of injection, aliquots of each strain will be thawed, combined into one tube and vortexed. Dilutions of each stock will then be prepared.

D2 Monoclonal Antibody 57-010 (INH-M01029, IAA2L1565)

The 57-010 monoclonal antibody ($IgG_1$ subtype) was purified from serum free hybridoma culture medium using protein G affinity chromatography. The material was reported to be at a concentration of 9.7 mg/ml with an endotoxin concentration of 1.0 EU/mg of protein. The material was stored refrigerated at 4° C. On the day of injection, the material will be diluted to 0.6 mg/ml and 0.5 ml will be administered via an intraperitoneal injection to the appropriate group of animals. The final dose that will be administered will be 0.8 mg of IgG. The hybridoma cell line producing monoclonal antibody 57-010 was deposited on Dec. 20, 2005 in the American Type Culture Collection (ATCC) Depository, 10801 University Boulevard, Manassas, Va. 20110-2209, and was given Patent Deposit Designation PTA-7283.

FnbpA Monoclonal Antibody 43-677 (INH-M01030, IAA2A2004)

The 43-677 monoclonal antibody ($IgG_1$ subtype) was purified from serum free hybridoma culture medium using protein G affinity chromatography. The material was reported to be at a concentration of 8.3 mg/ml with an endotoxin concentration of 1.0 EU/mg of protein. The material was stored refrigerated at 4° C. On the day of injection, the material will be diluted to 0.6 mg/ml and 0.5 ml will be administered via an intraperitoneal injection to the appropriate group of animals. The final dose that will be administered will be 0.8 mg of IgG.

Control CRL 1771 Monoclonal Antibody (INH-M000029, LN: IAA2E1337)

The CRL 1771 monoclonal antibody ($IgG_1$ subtype) was purified from serum free hybridoma culture medium using protein G affinity chromatography. The material was reported to be at a concentration of 5.0 mg/ml with an endotoxin concentration of 0.2 EU/mg of protein. The material was stored refrigerated at 4° C. On the day of injection, the material will be diluted 0.6 mg/ml and 0.5 ml will be administered via an intraperitoneal injection. The final dose that will be administered will be 0.8 mg of IgG.

Housing, Food, Water and Environment

Upon receipt, all animals were examined and group housed (5/cage) in polycarbonate shoebox style cages with absorbent bed-o-cobb bedding. All animals have free access to feed (Harlan/Teklad Mouse Pelleted Diet #7012) and tap water with a 12-hour light-dark cycle. All aspects of the animal care and the required husbandry conditions will be in accordance with the NIH *Guide for the Care and Use of Laboratory Animals.*

Identification and Randomization

All mice were uniquely identified by tail tattoo before treatment. Prior to treatment, the mice were individually weighed and their health re-evaluated. Mice were assigned to treatment groups based on randomization by stratified body weights.

Figure 3:
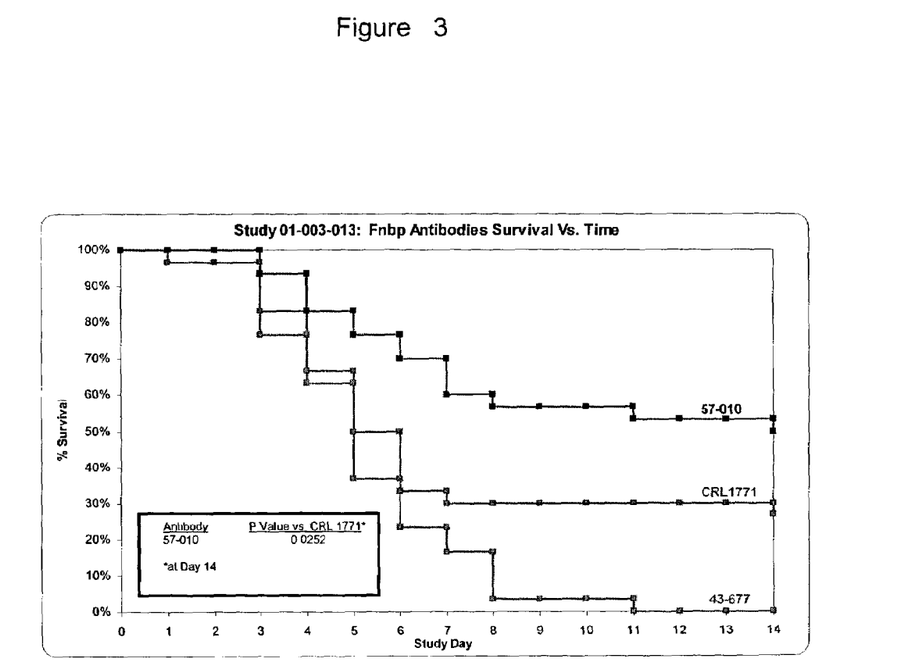
FIG. 3 is a graph depicting the percent survival of mice after treatment with 57-010, or a mouse IgG1 control (CRL 1771) or a FnbpA monoclonal antibody 43-677 after challenge with the S. aureus strain 67-0 in a murine model of S. aureus-induced sepsis.

The data in FIG. 3 demonstrate the therapeutic value of an anti-D2 antibody such as 57-010 compared with an isotype control (CRL 1771) as well as a specific control (43-677) that recognizes FnbpA at a site (A domain) independent of the D repeat region.

What is claimed is:

1. A monoclonal antibody that binds to the same epitope that is recognized by monoclonal antibody 57-010 as deposited with the American Type Culture Collection and assigned accession number PTA-7283.

2. An antibody according to claim 1 wherein the monoclonal antibody is raised against a peptide from the D2 region of fibronectin binding protein B (FnbpB) from *S. aureus*.

3. An antibody according to claim 1 wherein the monoclonal antibody is raised against a peptide comprising the first 30 amino acids of the D2 region of fibronectin binding protein B (FnbpB) from *S. aureus*.

4. An antibody according to claim 1, wherein said antibody treats *S. aureus* infection in a human or animal.

5. An antibody according to claim 1, wherein said antibody inhibits binding of staphylococcal bacteria to fibronectin.

6. An antibody according to claim 1, wherein said antibody is suitable for parenteral, oral, intranasal, subcutaneous, aerosolized or intravenous administration in a human or animal.

7. An antibody according to claim 1 wherein the monoclonal antibody is of a type selected from the group consisting of murine, chimeric, humanized and human monoclonal antibodies.

8. An antibody according to claim 1 wherein the antibody is a single chain monoclonal antibody.

9. An antibody according to claim 1 which comprises an antibody fragment having the same binding specificity of an antibody which binds to a *S. aureus* Fnbp protein.

10. An antibody according to claim 1 that is raised against a peptide having the amino acid sequence selected from the group consisting of SEQ ID NO:1 and SEQ ID NO:2.

11. Isolated antisera containing an antibody according to claim 1.

12. A diagnostic kit comprising an antibody according to claim 1 and means for detecting binding by that antibody.

13. A diagnostic kit according to claim 12 wherein said means for detecting binding comprises a detectable label that is linked to said antibody.

14. A method of diagnosing an infection of *S. aureus* comprising adding an antibody according to claim 1 to a sample suspected of being infected with *S. aureus*, and determining if antibodies have bound to the *S. aureus* in the sample.

15. A pharmaceutical composition comprising the antibody of claim 1 further comprising a pharmaceutically acceptable vehicle, carrier or excipient.

16. A pharmaceutical composition according to claim 15 further comprising a physiologically acceptable antibiotic.

17. A method of treating an infection of *S. aureus* comprising administering to a human or animal patient an effective amount of an antibody according to claim 1.

18. An antibody according to claim 1 which is capable of specifically binding to a peptide of the D2 region of the *S. aureus* FnbpB protein.

* * * * *